United States Patent [19]

Alexander

[11] Patent Number: 5,275,057
[45] Date of Patent: Jan. 4, 1994

[54] CLIP GAGE ATTACHMENT FOR FRICTIONLESS MEASUREMENT OF DISPLACEMENT DURING HIGH-TEMPERATURE MECHANICAL TESTING

[75] Inventor: David J. Alexander, Oak Ridge, Tenn.

[73] Assignee: Martin Marietta Energy Systems, Inc., Oak Ridge, Tenn.

[21] Appl. No.: 932,477

[22] Filed: Aug. 20, 1992

[51] Int. Cl.$^5$ ............................................. G01N 3/08
[52] U.S. Cl. ...................................... 73/799; 33/790; 374/49
[58] Field of Search ................... 73/799, 826; 374/46, 374/47, 48, 49, 50, 51; 33/787, 790

[56] References Cited

U.S. PATENT DOCUMENTS 5,083,465  1/1992  Myers ................................... 73/862

*Primary Examiner*—Jerry W. Myracle
*Attorney, Agent, or Firm*—James M. Spicer; Harold W. Adams

[57] ABSTRACT

An attachment for placement between a test specimen and a remote clip gage extensometer providing improved fracture toughness tests of materials at elevated temperature. Using a cylindrical tube and axial rod in new relationship, the device transfers the displacement signal of the fracture toughness test specimen directly to a clip gage extensometer located outside the high temperature furnace. Virtually frictionless operation is assured by having the test specimen center one end of the rod in one end of the tube, while the clip gage extensometer arms center the other end of the rod in the other end of the tube. By providing positive control over both ends of both rod and tube, the attachment may be operated in orientations other than vertical.

5 Claims, 1 Drawing Sheet

CLIP GAGE ATTACHMENT FOR FRICTIONLESS MEASUREMENT OF DISPLACEMENT DURING HIGH-TEMPERATURE MECHANICAL TESTING

This invention was made with Government support. It was funded by the U.S. Department of Energy, Assistant Secretary for Conservation and Renewable Energy, Office of Industrial Technologies, Advanced Industrial Concepts (AIC) Materials Program, under contract no. DE-AC05-84OR21400 with Martin Marietta Energy Systems, Inc. The Government has certain rights in this invention.

FIELD OF THE INVENTION

The invention relates to attachments for transmission of displacement, i.e., linear distance, from a specimen to an electrical detector. More particularly, the invention relates to a device which allows a clip gage extensometer to be located outside a high temperature region during fracture toughness tests. More particularly still, the invention relates to a parallel linkage device that hangs from a test specimen and mounts a clip gage extensometer, resulting in virtually frictionless transmission of the specimen displacement to the extensometer.

BACKGROUND OF THE INVENTION

The standard method for measuring linear displacement during room temperature fracture toughness tests is a clip gage extensometer instrumented with strain gages. The displacement is measured to allow the energy input into the specimen to be calculated. Also, periodic partial unloadings are made during the test. The slope of the load versus displacement curve is used to calculate the length of the crack throughout the test. This technique is referred to as the unloading compliance method.

For testing at elevated temperatures, the strain gages used within a clip gage extensometer would be destroyed. One solution to the problem of high temperature fracture toughness tests is to use a capacitance gage which can operate inside the furnace. The purpose of the attachment is to convey the linear displacement information from the deforming test specimen to an electrical sensor located out of the elevated temperature region. The type of sensor used with the prior art attachments is frequently, though not always, a linear variable differential transformer (LVDT).

Prior art

1. U.S. Pat. No. 4,848,161. Describes a tube-in-tube partially hanging type attachment for use in tensile testing. Uses an LVDT or super linear variable capacitance transducer (SLVC) for the sensor. Supports at the upper and lower ends of the outer tube maintain it in vertical orientation. The rigidity of the vertically-oriented tensile specimen is relied upon to maintain the inner tube in vertical orientation within the outer tube. Friction may be present in the LVDT sensor.

2. Proposed ASTM Standard Test Method for Measurement of Creep Crack Growth Rates in Metals, ASTM Designation: E 1457-92. Describes a rod-in-tube hanging type attachment for creep crack growth testing. Uses a direct current differential transformer (DCDT), capacitance gage, or LVDT for the sensor. Boron nitride bearings would generate excessive friction.

3. Extensometers, Product Bulletin from Applied Test Systems, Inc., Butler, Pa. Illustrates many hanging type attachments. Uses clip gage extensometers and LVDTs as sensors.

OBJECTS OF THE INVENTION

It is a first object of the present invention to provide an attachment for a mechanical test specimen in a high temperature furnace that transfers the deformation displacement of the specimen out of the furnace to a clip gage extensometer operating at room temperature.

A second object of the invention is to provide an attachment for hanging from a fracture toughness specimen being tested at elevated temperature, the attachment making it possible to conduct highly accurate measurements of displacement and unloading compliance.

Another object of the invention is to eliminate friction that leads to errors in measurement of unloading compliance of fracture toughness test specimens at elevated temperatures.

Another object of the invention is to provide an attachment for a clip gage extensometer that minimizes sliding friction by eliminating sources of such friction such as linear bearings and reliance on preset alignments.

SUMMARY OF THE INVENTION

The invention is an attachment for mounting on a test specimen having first and second closely-spaced opposed knife-edges between which displacement is to be measured, the attachment also mounting a clip gage extensometer, the attachment comprising:

a first extension arm for contacting the first knife-edge;

a second extension arm in noncontacting parallel relationship with the first extension arm, the second extension arm for contacting the second knife-edge;

a tube fixedly mounted at one of its ends to the first extension arm;

a rod fixedly mounted at one of its ends to the second extension arm, the rod extending through but not contacting the tube;

a means attached at the other end of the tube for mounting a third knife-edge in the same sense as the first knife-edge, this means also mounting the clip gage extensometer; and a means attached at the other end of the rod for mounting a fourth knife-edge in the same sense as the second knife-edge;

the first and second knife-edges acting to center the extension arm end of the rod within the extension arm end of the tube, and the arms of the clip gage extensometer contacting the third and fourth knife-edges, the extensometer arms acting to center the clip gage extensometer end of the rod within the clip gage extensometer end of the tube.

Figure 1:
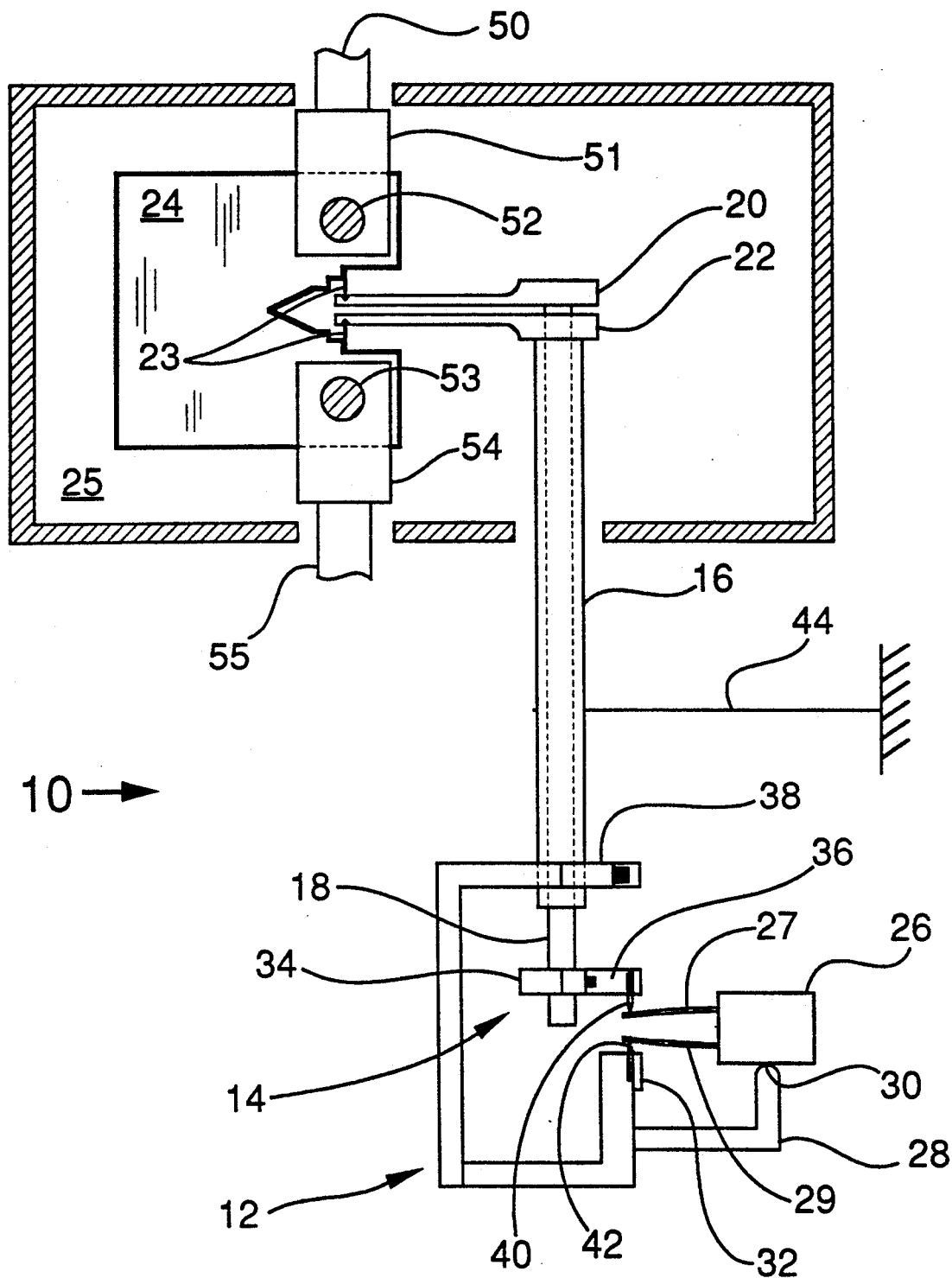
FIG. 1 is a view, partly in cross-section, of a mechanical test specimen attachment in accordance with a preferred embodiment of the invention.

For a better understanding of the present invention, together with other and further objects, advantages, and capabilities thereof, reference is made to the following disclosure and appended claims in connection with the above-described drawings.

DETAILED DESCRIPTION OF THE INVENTION

FIG. 1 shows the attachment 10 of this invention. The test specimen 24 is mounted in the usual way. It is held by clevis and pin arrangements 51, 52 and 54, 53 between a stationary pull rod 50 and active pull rod 55. The specimen is also fitted with hardened steel knife-edges 23 from which the deformation will be measured. In unloading compliance tests conducted at room temperature, it is standard practice to attach such knife-edges to the test specimen and locate the grooved arms of a clip gage extensometer directly on these knife-edges to measure the displacement of the test specimen.

As with some other attachments in the prior art, the invention relies on a coaxial rod and tube structure suspended from the test specimen to transmit the test specimen deformation displacement down the rod and tube to a location away from the furnace hot zone. It is customary practice to provide a wide clearance between the rod and tube to prevent them from contacting each other and producing friction. It is the lower portion of attachment 10 that differs from the prior art.

In FIG. 1, rod 18 is freely movable inside the tube 16. The rod 18 is rigidly attached to an upper extension arm 20, and the tube 16 is securely attached to a lower extension arm 22. The arms 20, 22 have V-grooves that seat on the knife-edges 23 of the test specimen 24. The elements 16, 18, 20, 22 operate within the hot zone of the furnace 25, and so are made of a heat-resistant high-strength material such as a nickel-base superalloy in order to remain rigid at elevated temperatures. Preferably, the tube 16 and rod 18 are made of the same or similar materials so as to have similar coefficients of thermal expansion.

The tube 16 is attached to a first frame member 12 with a tube clamp 38. This arrangement allows the vertical location of the frame 12 with respect to the tube 16 to be adjusted over a limited range by loosening the clamp 38, repositioning the frame 12, and re-tightening the clamp 38. A lower knife-edge holder 32 is attached to the frame 12 with its knife-edge 42 mounted in an upwardly-pointing direction. A second frame member 14, in turn, is attached to the rod 18. The frame member 14 comprises essentially an upper knife-edge holder 36 with downwardly directed knife-edge 40 attached to the rod 18 with a rod clamp 34. By this means, the vertical location of the upper knife-edge holder 36 may be adjusted slightly by loosening the clamp 34, repositioning the frame 14 on the rod 18, and re-tightening the clamp 34.

A clip gage extensometer 26 is supported on the first frame member 12 by means of a vertically adjustable stabilizing post 28 that has a point of contact 30 with the body of the extensometer 26. The arms 27, 29 of the clip gage extensometer 26 are precompressed and the V-grooves in the ends of arms 27, 29 are fitted in place on the knife-edges 40, 42, respectively. The restoring force of the compressed extensometer arms 27, 29 tries to force the knife-edges 40, 42 apart. This in turn forces the extension arms 20, 22 apart, allowing them to seat firmly on the knife-edges 23 of the test specimen 24. By this means, any deformation of the test specimen as recorded by the specimen knife-edges 23 is faithfully transferred by the rod 18 and tube 16 to the knife-edges 40, 42 where it is measured by the clip gage extensometer 26 operating at room temperature.

The materials used for the components at the lower end of the attachment 10 do not have to withstand elevated temperatures, so are made of any lightweight material such as aluminum. This will minimize the weight carried on the knife-edges 23. Besides supporting the clip gage extensometer 26, the stabilizing post 28 keeps the extensometer 26 from sagging, thereby steadying the extensometer and maintaining it in a generally horizontal orientation. This has the effect of stabilizing the position of the rod 18, i.e., the extensometer 26 acting through its arm 27 steadies the frame member 14 and consequently the lower end of the rod 18. The extensometer 26, in other words, keeps the rod 18 from pivoting from the specimen knife-edge, and hence maintains the generally concentric alignment of the rod 18 within the tube 16. Thus, there can be no contact or friction between any of the elements between the knife edges 23 and the knife-edges 40, 42.

All the weight of the attachment 10 is borne by the knife-edges 23. An alignment cord 44 attached between the tube 16 and a wall or other fixed end point is used to hold the attachment generally vertical to keep friction on the knife-edges 23 at a minimum. Of course, counterbalancing could be used on the attachment 10 to maintain it in generally vertical orientation on the knife-edges 23, but the alignment cord 44 may be preferable for this purpose since it does not add any weight to the attachment 10. While the attachment 10 is being described here in vertical orientation, it operates in any orientation. In nonvertical orientations, the cord 44 may also act to support some of the weight of the attachment 10. It will also be understood by those in the field that knife-edges could as well be attached to the arms of the clip gage extensometer 26 and V-grooves placed in the two frame members 12, 14 for attachment of the extensometer 26.

From the foregoing, it will be understood that the present invention features virtually no friction, which is the key to its success. The only friction in the system is the contact between the specimen knife-edges 23 and the V-grooves in the extension arms 20, 22; the contact between the frame knife-edges 40, 42 and the V-grooves in the extensometer arms 27, 29; and the point contact between the body of the clip gage extensometer 26 and the stabilizing post 28 at contact 30.

It will also be appreciated that the attachment operates in the same sense that the specimen is tested; that is, as the specimen opens, the attachment opens, and as the specimen closes, the attachment closes. A number of prior attachments operate in the opposite sense to the specimen; that is, they open as the specimen closes, and vice-versa. By operating in the same sense as the specimen, the clip gage extensometer can be precompressed to hold the extension arms on the specimen without having to use springs or other components which may introduce friction or cause alignment problems.

A calibration is performed before the attachment 10 is operated. To do the calibration, a micrometer is needed that has two knife-edges attached to it, similar to the knife-edges that would be attached to the test specimen. The first step is to suspend the lower extension arm 22 on the lower micrometer knife-edge, then spread the extension arms apart so that the upper extension arm 20 contacts the upper knife-edge on the micrometer. Then compress the arms 27, 29 of the clip gage extensometer 26 and insert extensometer 26 between the knife-edges 40, 42 attached to the rod 18 and tube 16. Next, the clip gage extensometer arms are released and allowed to spread apart. This forces the extension arms 20, 22 apart and forces them to seat securely on the knife-edges 23 attached to the micrometer. Then the alignment cord 44 is adjusted so that the attachment 10 hangs vertically. A series of known displacements are then set on the micrometer, and at each individual displacement, the voltage output from the clip gage extensometer 26 is recorded. This allows a calibration to be made between the voltage from the clip gage extensometer and the displacement of the knife-edges on the micrometer. This completes the calibration procedure of the attachment.

In operation, the attachment 10 is suspended from the lower of the knife-edges 23 attached to the test specimen 24. Then, the extension arms 20, 22 are spread apart so that the upper extension arm 20 contacts the upper of the knife-edges 23 on the test specimen. Holding the arms 20, 22 apart, the arms 27, 29 of the clip gage extensometer 26 are compressed and inserted between the knife-edges 40, 42 on the second and first frame members 14, 12 respectively. The arms 27, 29 are then allowed to spread apart which then forces the extension arms 20, 22 apart, allowing the attachment 10 to hang securely on the knife-edges 23 of the test specimen 24. Next, the alignment cord 44 is adjusted so that the attachment 10 hangs vertically. The furnace 25 is then carefully closed so as to not disturb the alignment of the attachment 10. The furnace 25 is then brought up to temperature and the specimen tested.

It will be understood that the attachment of this invention is not limited to the vertical orientation represented in FIG. 1 and described above. It will operate in any orientation. It would also be obvious to use other support arrangements such as three rods for the rod-in-tube arrangement described herein.

What has been described is an attachment for a clip gage extensometer for facilitating fracture toughness measurements of materials at elevated temperatures in air, gaseous or vacuum environments. It is capable of measuring unloading compliance at elevated temperature as well as one-way displacements such as tensile tests. The attachment may also be used for creep crack growth testing to measure displacement at high temperature over long periods of time.

It will also be appreciated that the invention facilitates the carrying-out of a potential drop test simultaneously with the measurement of linear displacement. The necessary electrical break in the attachment 10 for the potential drop test may be achieved by placing an electrical insulating material between the rod 18 and the rod clamp 34, or between tube 16 and tube clamp 38.

It should also be possible to use the attachment inverted, with the test specimen immersed in liquid medium such as corrosive liquid, and the clip gage extensometer away from the corrosive medium.

While there has been shown and described what are at present considered the preferred embodiments of the invention, it will be obvious to those skilled in the art that various changes and modifications can be made therein without departing from the scope of the inventions defined by the appended claims.

We claim:
1. An attachment for mounting on a test specimen having first and second closely-spaced opposed knife-edges between which displacement is to be measured, said attachment also mounting a clip gage extensometer, said attachment comprising:
a first extension arm for contacting said first knife-edge;
a second extension arm in noncontacting parallel relationship with said first extension arm, said second extension arm for contacting said second knife-edge;
a tube fixedly mounted at one of its ends to said first extension arm;
a rod fixedly mounted at one of its ends to said second extension arm, said rod extending through but not contacting said tube;
means attached at the other end of said tube for mounting a third knife-edge in the same sense as said first knife-edge, said means also mounting said clip gage extensometer; and
means attached at the other end of said rod for mounting a fourth knife-edge in the same sense as said second knife-edge;
said first and second knife-edges acting to center the extension arm end of said rod within the extension arm end of said tube, and the arms of said clip gage extensometer contacting said third and fourth knife-edges, said extensometer arms acting to center the clip gage extensometer end of said rod within the clip gage extensometer end of said tube.

2. The attachment of claim 1 further comprising an alignment cord connected between said attachment and a fixed end point for maintaining said attachment in a preferred orientation.

3. The attachment of claim 2 wherein said alignment cord also supports part of the weight of said attachment.

4. An attachment for hanging on a specimen having two closely-spaced knife-edges between which displacement is to be measured, and said attachment mounting a clip gage extensometer, said attachment comprising:
a first frame member;
a second frame member generally disposed within but not contacting said first frame member;
a tube adjustably mounted at one of its ends to said first frame member;
a first extension arm fixedly mounted at the other end of said tube;
a rod adjustably mounted at one of its ends to said second frame member, said rod extending through but not contacting said tube;
a second extension arm fixedly mounted at the other end of said rod; said second extension arm in parallel relationship to said first extension arm;
a knife-edge mounted on said first frame member;
a knife-edge mounted on said second frame member close-spaced to said knife-edge of said first frame member;
a stabilizing post fixedly attached to said first frame member;
said extension arms contacting said knife-edges of said specimen whereby said extension arm end of said rod is maintained generally centered within said extension arm end of said tube; and
the body of said clip gage extensometer rests on said stabilizing post, the clip gage extensometer arms contacting said knife-edge of said first frame member and said knife-edge of said second frame member whereby said clip gage extensometer arms maintain said frame end of said rod generally centered within said extension arm end of said tube.

5. The attachment of claim 4 further comprising an alignment cord connected between said attachment and a fixed end point for maintaining said attachment in a generally vertical orientation.

* * * * *